United States Patent
Fan et al.

(10) Patent No.: US 7,049,433 B2
(45) Date of Patent: *May 23, 2006

(54) GLUCOSAMINE AND METHOD OF MAKING GLUCOSAMINE FROM MICROBIAL BIOMASS

(75) Inventors: Weiyu Fan, Minnetonka, MN (US); John A. Bohlmann, Ottumwa, IA (US); James R. Trinkle, Bussey, IA (US); James Donald Steinke, Oskaloosa, IA (US); Ki-Oh Hwang, Oskaloosa, IA (US); Joseph P. Henning, Eddyville, IA (US)

(73) Assignee: Cargill, Incorporated, Wayzata, MN (US)

( * ) Notice: Subject to any disclaimer, the term of this patent is extended or adjusted under 35 U.S.C. 154(b) by 158 days.

This patent is subject to a terminal disclaimer.

(21) Appl. No.: 10/326,549

(22) Filed: Dec. 19, 2002

(65) Prior Publication Data
US 2003/0148998 A1    Aug. 7, 2003

Related U.S. Application Data

(63) Continuation of application No. 09/785,695, filed on Feb. 16, 2001, now abandoned.

(51) Int. Cl.
    C08B 37/00    (2006.01)
    C07H 5/04     (2006.01)
    A61K 31/70    (2006.01)
(52) U.S. Cl. .................. 536/55.2; 536/55.3; 514/62
(58) Field of Classification Search ............. 536/55.2, 536/55.3; 514/62
See application file for complete search history.

(56) References Cited

U.S. PATENT DOCUMENTS

| | | |
|---|---|---|
| 2,040,879 A | 5/1936 | Rigby |
| 3,232,836 A | 2/1966 | Carlozzi et al. |
| 3,632,754 A | 1/1972 | Balassa |
| 3,683,076 A | 8/1972 | Rovati |
| 3,903,268 A | 9/1975 | Balassa |
| 3,911,116 A | 10/1975 | Balassa |
| 3,914,413 A | 10/1975 | Balassa |
| 4,056,432 A | 11/1977 | Slagel et al. |
| 4,282,351 A | 8/1981 | Muzzarelli |
| 4,642,340 A | 2/1987 | Senin et al. |

(Continued)

FOREIGN PATENT DOCUMENTS

EP        566 349        10/1993

(Continued)

OTHER PUBLICATIONS

Kostina et al., "Chitin of mycelial fungi of the Penicillium genus," Prikl. Biokhim. Mikrobiol. Abstract (1978), 14(4), 586-593.

(Continued)

*Primary Examiner*—Shengjun Wang
(74) *Attorney, Agent, or Firm*—Klarquist Sparkman, LLP

(57) ABSTRACT

Glucosamine suitable for human or animal consumption is disclosed. The glucosamine is derived from microbial biomass containing chitin. Suitable starting materials include substantially uniform microbial fungal sources, such as fungal sources derived from *Aspergillus* sp., *Penicillium* sp., *Mucor* sp. and combinations thereof. Methods of producing glucosamine by acid hydrolysis of fermented fungal biomass are also disclosed.

13 Claims, 3 Drawing Sheets

U.S. PATENT DOCUMENTS

| | | | |
|---|---|---|---|
| 4,806,474 A | 2/1989 | Hershberger | |
| 4,886,541 A | 12/1989 | Hadwiger | |
| 4,948,881 A | 8/1990 | Naggi et al. | |
| 4,970,150 A | 11/1990 | Yaku et al. | |
| 4,983,304 A | 1/1991 | Tsugita et al. | 210/640 |
| 5,219,749 A | 6/1993 | Bouriotis et al. | |
| 5,232,842 A | 8/1993 | Park et al. | |
| 5,262,310 A | 11/1993 | Karube et al. | |
| 5,702,939 A | 12/1997 | Fujishima et al. | |
| 5,730,876 A | 3/1998 | You et al. | |
| 5,843,923 A | 12/1998 | Schleck et al. | |
| 5,902,801 A | 5/1999 | Schleck et al. | |
| 5,905,035 A | 5/1999 | Okada et al. | |
| 5,985,644 A | 11/1999 | Roseman et al. | |
| 5,998,173 A | 12/1999 | Haynes et al. | |
| 6,117,851 A | 9/2000 | Sherman et al. | |
| 6,248,570 B1 | 6/2001 | Michon et al. | |
| 6,333,399 B1 | 12/2001 | Teslenko et al. | |

FOREIGN PATENT DOCUMENTS

| | | |
|---|---|---|
| EP | 768 320 | 4/1997 |
| EP | 0 885 954 A1 | 12/1998 |
| EP | 997 480 | 5/2000 |
| GB | 458839 | 12/1936 |
| GB | 785525 | 10/1957 |
| GB | 833264 | 4/1960 |
| GB | 896940 | 5/1962 |
| JP | 55012109 | 1/1980 |
| JP | 62070401 A2 | 3/1987 |
| JP | 63097633 A2 | 4/1988 |
| JP | 63225602 A2 | 9/1988 |
| JP | 2149335 A2 | 6/1990 |
| JP | 2180903 A2 | 7/1990 |
| JP | 2200196 A2 | 8/1990 |
| JP | 2229832 A2 | 9/1990 |
| JP | 2258740 A2 | 10/1990 |
| JP | 5068580 A2 | 10/1993 |
| JP | 7330808 A2 | 12/1995 |
| JP | 8-41106 A | 2/1996 |
| JP | 10297913 A2 | 11/1998 |
| WO | WO 98/30713 | 7/1998 |
| WO | WO 98/42755 | 10/1998 |
| WO | 99 41294 | 8/1999 |
| WO | WO 00/04182 | 1/2000 |

OTHER PUBLICATIONS

Novikov, "Kinetics of formation of D-(+)- glucosamine in acid hydrolysis of chitin," Russian Journal Abstract (Sankt-Peterburg) (1999), 72(1), 147-152.

Yang et al., "Acidic hydrolysis and determination of fungal mycelium in cereals," Chinese Journal Abstract, Chinese Agricultural Chimical Society (1998) 36(6), 555-564.

Nilsson et al., "Chitin as an indicator of the biomass of two wood-decay fungi in relation to temperature, incubation time, and media composition," Abstract, Canadian Journal of Microbiology, (1998), vol. 44, No. 6, 575-581.

Plassard et al., "Estimation of mycelial growth of basidiomycetes by means of chitin determination," Abstract, Phytochemistry (Oxford) (1982), vol. 21, No. 2, 345-349.

Copy of glucosamine product label from Twinlab Flexi-licious (with shellfish allergy warning).

Copy of glucosamine product label from HyVee HealthMarket (with shellfish allergy warning).

Copy of glucosamine product label from Osteo Bi-flex (2 pages) (with shellfish allergy warning).

Jeremy Appleton, *Inadequate Screening of Imported Food and Dietary Supplements*, 2 Integrative Medicine, 58-65 (available at www.ifr.bbsrc.ac.uk/protall/infosheet.htm, Feb./Mar. 2003).

Xianchang Gong, *Heavy Metal Contaminates in the Glucosamine Product* (a paper regarding a crab shell glucosamine product) (date unknown).

Department of Health and Human Services, *FDA Increases Sampling of Imported Shrimp and Crayfish*, FDA News (2002) (available at www.fda.gov.bbs.topics/News/2002/New00815.html, last visited Oct. 18, 2002).

Federal Trade Commission, *Shark Cartilage Receives 10M Draft Monograph*, FTC Notice (2002) (available at www.ftc.gov/opa/2002/09/fdacomments.htm, as of Sep. 2002).

Aldrich, Catalog Hand book of Fine Chemicals, p. 756 (1996).

Alonso, I. et al., "Determination of the Degree of Acetylation of Chitin and Chitosan by Thermal Analysis," *Journal of Thermal Analysis*, vol. 28, pp. 189-193 (1983).

Arcidiacono, S. et al., "Molecular Weight Distribution of Chitosan isolated from *Mucor rouxii* under Different Culture and Processing Conditions," *Biotechnology and Bioengineering*, vol. 39, pp. 281-286 (1992).

Atrih, A. et al., "Analysis of Peptidoglycan Structure from Vegetative Cells of *Bacillus subtilis* 168 and Role of PBP 5 in Peptidoglycan Maturation," *Journal of Bacteriology*, vol. 181, No. 13, pp. 3956-3966 (Jul. 1999).

Bartnicki-Garcia, S., "Cell Wall Chemistry, Morphogenesis, and Taxonomy of Fungi," *Chemistry of Fungal Cell Wall*, pp. 87-108 (1968).

Benjakul, S. et al., "Improvement of Deacetylation of Chitin from Black Tiger Shrimp (*Penaeus monodon*) Carapace and Shell," *ASEAN Food Journal*, vol. 9, No. 4, pp. 136-140 (1994).

Beri, R., et al., "Characterization of Chitosans via Coupled Size-Exclusion Chromatography and Multiple-Angle Laser Light-Scattering Technique," *Carbohydrate Research*, vol. 238, pp. 11-26 (1993).

Biermann, C., "Hydrolysis and Other Cleavage of Glycosidic Linkages," Chapter 3, pp. 29-41 (Date Unknown).

Carlson, T. et al., "Chitin/Chitosan Extraction from *A. Niger* Mycelium," *Cargill Central Research*, 16 pages (Aug. 1997).

"Chitin/Chitosan Specifications," *Biopolymer Engineering, Inc.*, http://www.biopolymer.com/spec.htm, 1 page (Date printed Mar. 4, 1999).

Davies, D., et al., "Determination of the Degree of Acetylation of Chitin and Chitosan," *Methods in Enzymology*, vol. 161, Part B, pp. 442-446 (1988).

Deal, C. et al., "Nutraceuticals as Therapeutic Agents in Osteoarthritis. The Role of Glucosamine, Chondroitin Sulfate, and Collagen Hydrolysate," *Osteoarthritis*, vol. 25, No. 2, pp. 379-395 (May 1999).

Domszy, J. et al., "Evaluation of Infrared Spectroscopic Techniques for Analyzing Chitosan," *Makromal. Chem.*, vol. 186, pp. 1671-1677 (1985).

Farkas, V., "Fungal Cell Walls: Their Structure, Biosynthesis and Biotechnological Aspects," *Acta Biotechnol.*, vol. 10, No. 3, pp. 225-238 (1990).

Ferrer, J., "Acid Hydrolysis of Shrimp-Shell Wastes and the Production of Single Cell Protein from the Hydrolysate," *Bioresourcc Technology*, vol. 57, pp. 55-60 (1996).

Fleet, G. et al., "17 Fungal Glucans—Structure and Metabolism," *Encyclopedia of Plant Physiology*, vol. 13B, New Series, pp. 416-440 (1981).

"The Fungal Cell," Chapter 2, pp. 22-39 (Date Unknown).

Gassner, G. et al., "Teichuronic Acid Reducing Terminal N-Acetylglucosamine Residue Linked by Phosphodiester to Peptidoglycan of *Micrococcus luteus*," *J. Bacteriol.*, vol. 172, No. 5. pp. 2273-2279 (May 1990).

"Glucosamine Hydrochloride," *Pharmacopeial Forum*, vol. 26, No. 5, pp. 1449-1450 (Sep.-Oct. 2000).

Gobin, P. et al., "Structural Chemistry of Fungal Polysaccharides," pp. 367-417 (1968).

Jacobson, R., "Berichte der Deutschen Chemischen Gesellschaft," pp. 2192-2200 (1898) (German).

Johnston, I., "The Composition of the Cell Wall of *Asperigillus niger*," *Biochem. J.*, vol. 96, pp. 651-658 (1965).

Kimura, K. et al, "Determination of the Mode of Hydrolysis of Chitooligosaccharides by Chitosanase Derived from *Aspergillus Oryzae* by Thin Layer Chromatography," *Chemistry Letters*, pp. 223-226 (1992).

Kurita, K., "Controlled Functionalization of the Polysaccharide Chitin," *Prog. Polym. Sci.*, vol. 26, pp. 1921-1971 (2001).

Kurita, K. et al., "Studies on Chitin, 3, Preparation of Pure Chitin, Poly(N-acetyl-D-glucosamine), from the Water-Soluble Chitin," *Makromal. Chem.*, vol. 178, pp. 2595-2602 (1977).

Kurita, K. et al., "Studies on Chitin, 4, Evidence for Formation of Block and Random Copolymers of N-Acetyl-D-glucosamine and D-Glucosamine by Hetero- and Homogeneous Hydrolyses," *Makromol. Chem.*, vol. 178, pp. 3197-3202 (1977).

Maghami, G. et al., "Evaluation of the Viscometric Constants for Chitosan," *Makromol. Chem.*, vol. 189, pp. 195-200 (1988).

Maitre, N. et al., "Primary T-Cell and Activated Macrophage Response Associated with Tumor Protection Using Peptide/Poly-N-Acetyl Glucosamine Vaccination," *Clinical Cancer Research*, vol. 5, pp. 1173-1182 (May 1999).

Mima, S. et al., "Highly Deacetylated Chitosan and Its Properties," *Journal of Applied Polymer Sciences*, vol. 28, pp. 1909-1917 (1983).

Muzzarelli, R. et al., "Chelating, Film-Forming, and Coagulating Ability of the Citosan-Glucan Complex from *Aspergillus niger* Industrial Wastes," *Biotechnology and Bioengineering*, vol. XXII, pp. 885-896 (1980).

Nanjo, F. et al., "Purification, Properties, and Transglycosylation Reaction of β-N-Acetylhexosaminidase from *Nocardia orientalis*," *Agric. Biol. Chem.*, vol. 54, No. 4, pp. 899-906 (1990).

Nanjo, F. et al., "Purification and Characterization of an Exo-β-D-glucosaminidase, a Novel Type of Enzyme, from *Nocardia orientalis*," *The Journal of Biological Chemistry*, vol. 265, No. 17, pp. 10088-10094 (Jun. 15, 1990).

Nanjo, F. et al., "Enzymatic Method for Determination of the Degree of Deacetylation of Chitosan," *Analytical Biochemistry*, vol. 193, pp. 164-167 (1971).

Nikolaeva et al., CAPLUS Abstract, AN 1968:62461 (1968).

Nguyen, T. et al., "Composition of the Cell Walls of Several Yeast Species," *Abstract*, vol. 50, No. 2, pp. 206-212 (1998).

Niola, F. et al., "A Rapid Method for the Determination of the Degree of N-acetylation of chitin-chitosan samples by acid hydrolysis and HPLC," *Carbohydrate Research*, vol. 238, pp. 1-9 (1993).

No, H. et al. "Preparation and Characterization of Chitin and Chitosan—A Review," *Journal of Aquatic Food Product Technology*, vol. 4, No. 2, pp. 27-51 (1995).

Nogawa, M. et al., "Purification and Characterization of Exo-β-D-Glucosaminidase from a Cellulolytic Fungas, *Trichoderma reesei* PC-3-7," *Appl. Environ. Microbiol.*, vol. 64, No., 3, pp. 890-895 (Mar. 1998).

Novikov, V. et al., "Synthesis of D(+)-Glucosamine Hydrochloride," *Russian Journal of Applied Chemistry*, vol. 70, No. 9, pp. 1467-1470 (1997).

Ottoy, M. et al., "Preparative and Analytical Size-exclusion Chromatography of Chitosans," *Carbohydrate Polymers*, vol. 31, pp. 253-261 (1996).

Pelletier, A. et al., "Chitin/Chitosan Transformation by Thermo-Mechano-Chemical Treatment Including Characterization by Enzymatic Depolymerization," *Biotechnology and Bioengineering*, vol. 36, pp. 310-315 (1990).

Rege, P. et al. "Chitosan Processing: Influence of Process Parameters During Acidic and Alkaline Hydrolysis and Effect of the Processing Sequence on the Resultant Chitosan's Properties," *Carbohydrate Research*, vol. 321, Nos., 3-4, pp. 235-245 (Oct. 15, 1999).

Roberts, G. et al., "Determination of the Viscomtric Constants for Chitosan," *Int. J. Biol.*, vol. 4, pp. 374-377 (Oct. 1982).

Rokem, J. et al., "Degradation of Fungal Cell Walls Taking into Consideration the Polysaccharide Composition," *Enzyme Microb. Technol.*, vol. 8, No. 10, pp. 588-592 (Oct. 1986) (Abstract).

Ruiz-Herrera, J., "Chemical Components of the Cell Wall of *Aspergillus Species*," *Archives of Biochemistry and Biophysics*, vol. 122, pp. 118-125 (1967).

Sabnis, S. et al., "Improved Infrared Spectroscopic Method for the Analysis of Degree of N-deacetylation of Chitosan," *Polymer Bulletin*, vol. 39, pp. 67-71 (1997).

Sakai, K. et al., "Purification and Hydrolytic Action of a Chitosanase from *Nocardia orientalis*," *Biochimica et Biophysica Acta.*, vol. 1079, pp. 65-72 (1991).

Sannan, T. et al., "Studies on Chitin, 2, Effect of Deacetylation on Solubility," *Makromol. Chem.*, vol. 177. pp. 3589-3600 (1976).

Shahidi, F. et al., "Food Applications of Chitin and Chitosans," *Trends in Food Science & Technology*, vol. 10, pp. 37-51 (1999).

Shu, C-K, "Degradation Products Formed from Glucosamine in Water," *J. Agric. Food Chem.*, vol. 46, pp. 1129-1131 (1998).

Sigma, Biochemicals and Reagents, p. 461 (2000).

Stagg, C. et al., The Characterization of a Chitin-Associated D-Glucan from the Cell Walls of *Aspergillus Niger*, vol. 320, pp. 64-72 (1973).

Stainer, R. et al., "The Microbial World," *Prentice-Hall, Inc.*, pp. 332-336 (1970).

Tan, S. et al., "The Degree of Deacetylation of Chitosan: Advocating the First Derivative UV-spectrophotometry Method of Determination," *Talanta*, vol. 45, pp. 713-719 (1998).

Wessels, J. et al., "15 Fungal Cell Walls: A Survey," *Plant Carbohydrates II, Extracellular Carbohydrates*, pp. 352-394 (1981).

Wu, A. et al., "Determination of Molecular-Weight Distribution of Chitosan by High-performance Liquid Chromatography," *Journal of Chromatography*, vol. 128, pp. 87-99 (1976).

Cargill Acidulants, "Proposal for making a "Substantial Equivalence" notification for Non-Shellfish Glucosamine Hydrochloride under Regulation (EC) No. 258/97 for the European Parliament and the Council of Jan. 27, 1997 concerning novel foods and novel food ingredients," Feb. 5, 2004.

Cargill, Incorporated, "Gras Notification for Regenasure™ Glucosamine Hydrochloride," Apr. 6, 2004.

Xin et al., "Primary study on the production of chitosan by the method of culturing microorganism," *Food Science*, p. 22(3pp.), Jul. 1997 ( and a partial English translation).

GLUCOSAMINE AND METHOD OF MAKING GLUCOSAMINE FROM MICROBIAL BIOMASS

PRIORITY CLAIM

This application is a continuation of pending U.S. patent application Ser. No. 09/785,695, filed Feb. 16, 2001 now abandoned.

FIELD

The present invention is directed to glucosamine compositions and to methods of making glucosamine compositions.

BACKGROUND

Glucosamine is a nutraceutical supplement that has been shown to provide significant therapeutic relief for arthritis and joint pain. Although the mechanism is not entirely known, it is believed that glucosamine functions to aid in restoration of the cartilage to relieve inflammation in the joints, thereby providing significant benefit to patients.

Presently, glucosamine is primarily derived from harvested natural sources, such as shellfish and other aquatic organisms. Components of the shell or exoskeleton of these organisms are converted into glucosamine using various production techniques. These natural sources are acceptable for producing glucosamine for some applications, but they have limitations. These limitations include the fact that wild shellfish can have significant variations in their composition because they grow naturally under uncontrolled circumstances. The shellfish can vary in such aspects as their size and composition depending upon the growing conditions as well as their species. Also, without control over the growing conditions, the shellfish can be exposed to environmental contaminants, including heavy metals, that can be retained in glucosamine or other products produced from the shellfish. Shellfish harvests are often seasonal, and thus the supply and price of shellfish shows significant variation over time.

A further concern with glucosamine derived from shellfish is that significant portions of the human population have shellfish allergies and are unable to use products that contain ingredients derived from shellfish. Highly processed materials, such as glucosamine, do not necessarily provide any allergic risk when prepared properly; but a concern remains that hyper allergic individuals will still be allergic to even minute traces of allergens present from the original shellfish. Even if no such allergens are present, glucosamine derived from shellfish can pose a concern to individuals who are allergic to shellfish because individual consumers are not necessarily aware of whether or not all of the allergens have been removed.

An additional problem associated with existing sources of shellfish-derived glucosamine is that some of the shellfish supply is harvested from the seas and oceans of the world. Excessive harvest of shellfish could have a great negative environmental impact. Thus, it is believed that some consumers would prefer to use glucosamine that is not harvested at the expense of sea life. Even if the environmental impact of harvesting shellfish is not negative, there remains concern that the supply of wild shellfish is limited in quantity and inconsistent in quantity from year to year.

Therefore, a need exists for a source of safe, consistent, high quality glucosamine that can be created economically and with a minimum of environmental impact.

SUMMARY

The present invention is directed to glucosamine, including glucosamine-containing material suitable for human or animal consumption. Glucosamine of the present invention is derived from fermented fungal biomass containing chitin. Suitable starting materials include substantially uniform microbial fungal sources, such as fungal sources derived from *Aspergillus* sp., *Penicillium* sp., *Mucor* sp., and combinations thereof. Use of a fungal biomass results in a high quality product that produces generally uniform glucosamine having low levels of impurities. The glucosamine of the present invention normally has relatively low ash content, and low heavy metal content. In addition, as a product of fungal biomass, the glucosamine does not pose a hazard to persons who have shellfish allergies.

The present invention is also directed to methods of producing glucosamine by acid hydrolysis of fermented fungal biomass. The methods of obtaining glucosamine from microbial biomass include reacting chitin-containing biomass in an acidic solution, in particular reacting the chitin-containing biomass in acid at an elevated temperature.

Other features and advantages of the invention will be apparent from the following detailed description of the invention and the claims. The above summary of principles of the disclosure is not intended to describe each illustrated embodiment or every implementation of the present disclosure. The detailed description that follows more particularly exemplifies certain embodiments utilizing the principles disclosed herein.

DRAWINGS

The invention will be more fully explained with reference to the following drawings, in which.

Figure 1:
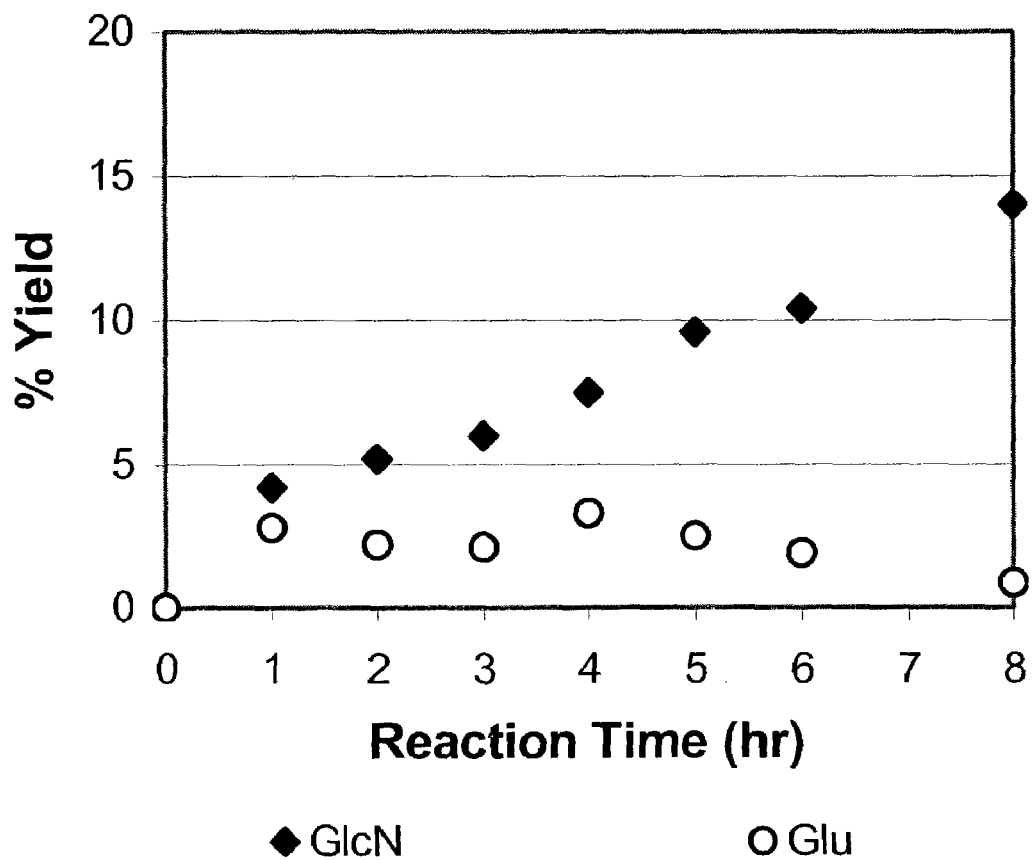
FIG. 1 is chart showing the percent yield of glucosamine over time of an example method of making glucosamine in accordance with the invention.

While principles of the invention are amenable to various modifications and alternative forms, specifics thereof have been shown by way of example and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The present invention is directed to glucosamine, including glucosamine-containing material suitable for human or animal consumption. The glucosamine is derived from chitin present in various types of fungal biomass. Chitin is a natural polysaccharide, with the structure of an unbranched polymer of 2-acetoamido-2-deoxy-D-glucose (N-acetyl-D-glucosamine). This formula can be represented by the general repeating structure:

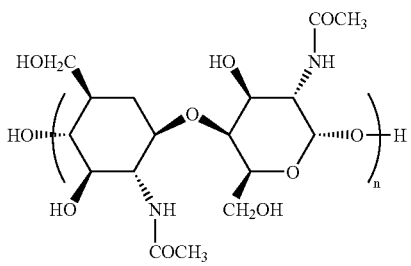

Chitin is typically an amorphous solid that is largely insoluble in water, dilute acids, and alkali. Although chitin has various commercial applications, greater commercial utility can be found by transforming the polymeric structure into individual components of 2-amino-2-deoxy-D-glucose, which is known as glucosamine. Structurally, glucosamine is modified glucose with an amine group replacing the OH group found on carbon two (C-2). The general structure is:

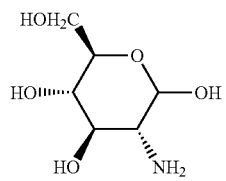

As stated above, glucosamine of the present invention is derived from fermented fungal biomass containing chitin. Suitable starting materials include substantially uniform microbial fungal sources, such as fungal sources derived from *Aspergillus* sp., *Penicillium* sp., *Mucor* sp. and combinations thereof. Use of a fungal biomass results in a high quality product that produces a generally uniform glucosamine having low levels of impurities. The glucosamine of the present invention normally has relatively low ash content, and low heavy metals content. In addition, as a product of fungal biomass, the glucosamine does not pose a hazard to persons who have shellfish allergies.

The glucosamine composition, starting materials, and production methods will now be described in greater detail A. Glucosamine The glucosamine of the present invention is derived from relatively uniform fungal biomass sources, and thus typically has a generally uniform composition. Depending upon the methodology used to purify the glucosamine or desired glucosamine salt; the resulting glucosamine containing composition can be produced with varying levels of purity, including compositions that exceed 95 percent purity, 98 percent purity, and even 99.8 percent purity. The glucosamine compositions can also contain additional ingredients, such as additional salts. In such circumstances the overall purity of the desired composition relative to undesirable impurities can be maintained at levels that exceed 95 percent purity, 98 percent purity, and even 99.8 percent purity.

The glucosamine of the present invention has the general formula represented below:

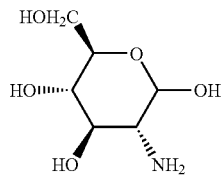

This general formula can vary depending upon the presence of various salts of the glucosamine, including citrate, acetate, phosphate, sulfate, chloride, lactate, gluconate, etc. Also, the glucosamine can be substituted or modified without diverging from the scope of the invention. Thus, as used herein, the term glucosamine refers to the various forms of glucosamine, including salt complexes and substituted glucosamine.

The glucosamine is normally of high purity, but can contain other ingredients, including glucose, unreacted chitin, and other materials. Preferably the glucosamine contains less than 10 percent glucose, more preferably less than 5 percent glucose, and even more preferably less than 2 percent glucose.

The glucosamine of the present invention has a relatively low ash content. The ash content is usually less than 5 percent, more typically less than 2 percent, and can even be less than 1 percent in some implementations. Heavy metal content is normally similarly low, typically well below 100 parts per million, more typically below 50 parts per million, even more typically below 20 parts per million. In certain embodiments this level is below 10 parts per million. The glucosamine can have a positive specific rotation, such as a positive 69 to 74 degree specific rotation for the glucosamine hydrochloride salt.

The glucosamine of the invention is usually relatively white in its purified dry form, but colorless when dissolved in an aqueous solution. In one example, a 20 percent by weight solution of the glucosamine has an American Public Health Association (APHA) color of less than 50.

B. Microbial Fungal Biomass Starting Materials

Suitable starting materials include substantially uniform microbial biomass sources, typically fungal biomass, such as filamentous fungi having greater than 10 percent chitin by total dry cell weight, such as fungal sources derived from *Aspergillus* sp., *Penicillium* sp., *Mucor* sp. Suitable fungal biomasses include *Aspergillus niger, Aspergillus terreus, Aspergillus oryzae, Mucor rouxii, Penicillium chrysogenum, Penicillium notatum, Saccharomyces cerevisiae; Saccharomyces uvarum*; and in particular *Candida guillermondi, Aspergillus niger*, and *Aspergillus terreus*. The biomass is usually recovered from a commercial fermentation reaction, such as the commercial production of organic acids, including citric acid. Also, the biomass suitable for production of glucosamine can be generated specifically for this process and not as a byproduct of other processes. As used herein, the term microbial does not include phyto-plankton and crustaceans or mollusks.

The invention is particularly well suited to uses where the chitin levels in the biomass exceed 5 percent of the dry biomass weight. Such biomass usually has between 5 and 25 percent chitin, and can have from 10 to 20 percent chitin, based upon dry weight of the biomass. Also, in order to prepare the highest quality glucosamine, it is sometimes desirable that the microbial biomass be produced in a substantially controlled manner having relatively uniform temperature and nutrient levels during the growth of the biomass.

C. Glucosamine Production Methods

The present invention is also directed to methods of forming glucosamine, including formation from acid hydrolysis of fermented fungal biomass. The acid hydrolysis breaks the ether linkages and deacetylates the chitin molecule to generate free glucosamine. Acid hydrolysis is strong enough to break the chitin into glucosamine, but leaves the glucosamine molecule substantially intact. The hydrolysis reaction conditions have the added advantage of breaking down some of the other components (such glucans, proteins, and lipids) that exist in the fungal biomass. Typically, such acid hydrolysis is performed by treating the fungal biomass for greater than 4 hours in a strong acid solution.

Glucosamine production usually includes the steps of providing chitin-containing biomass, reacting the chitin-containing biomass in an acidic solution to form glucosamine, and separating the glucosamine from the acidic solution. The reaction typically has a yield of glucosamine of greater than 50 percent of total chitin content of the fungal biomass starting material.

Strong acids can be used to hydrolyze the fungal biomass, including acids of concentrations less than 50 percent, and more commonly from 5 to 25 percent. Suitable strong acids include hydrochloric, sulfuric, phosphoric, and citric acid at appropriate levels.

The glucosamine forming reaction is normally conducted with 5 to 20 percent acid, 2 to 50 percent pretreated biomass (based upon dry weight, although the biomass is typically processed with water present), and 35 to 93 percent water. In certain implementations the reaction mixture comprises from 8 to 12 percent hydrochloric acid, from 4 to 8 percent biomass (based upon dry weight), and from 80 to 90 percent water.

The mixture containing the biomass, acid, and water is heated and maintained at an elevated temperature. The mixture is usually heated to a temperature at or near its boiling point and maintained under reflux conditions for greater than 5 hours, more typically greater than 8 hours, and usually less than 16 hours. It is desirable to have the reaction continue long enough to have a complete breakdown of the chitin, but not take so long as to be inefficient or to excessively decompose the glucosamine.

Reaction in the acid solution produces glucosamine, but subsequent purification steps are typically necessary to produce a satisfactory product. A first purification step normally includes filtration to remove particulate impurities, resulting in a substantially clear filtrate. This filtrate normally contains glucosamine, as well as small quantities of glucose and other sugars. An evaporative step can subsequently be performed to concentrate the glucosamine and possibly remove some of the acid, which can be recycled and reused. The mixture can be concentrated by evaporation, and the glucosamine can be precipitated out as purified solids by either adding ethanol to the concentrated mixture or continuing the evaporation to its solubility limits.

The glucosamine can be recovered by filtration or centrifugation, followed by drying. The dried glucosamine is optionally further purified to remove any residual sugar. One method of removing these excess sugars is by dissolving the glucosamine in water and adding ethanol, which precipitates the glucosamine at greater purity. Alternatively, the solution can be purified by electro dialysis, chromatography, membrane filtration, etc. The glucosamine is optionally decolorized with ethanol, carbon, or other suitable material and method.

In addition to the steps described above, the biomass can initially be treated to remove some impurities or to improve glucosamine production. These treatments can include heating the biomass, adding digestive enzymes, mixing with an acid or base, mechanical agitation, or dewatering by compression. One particularly suitable treatment is pretreating the biomass in the presence of sodium hydroxide. In certain implementations a concentration of less than 10 percent sodium hydroxide is added to the fungal biomass, which is heated to an elevated temperature for a period sufficient to remove a considerable portion of the non-chitin containing material. This period is normally less than two hours. One specific example of this pretreatment method requires heating the fungal biomass to 100 to 125° C. in a 2 to 8 percent solution of sodium hydroxide for 20 to 60 minutes. This step hydrolyzes some protein and glucan in the biomass, the byproducts of which are optionally removed by filtration. The filtration step is followed to remove soluble proteins, amino acids, etc. In specific implementations of the invention, the washed and pretreated biomass contains greater than 50 percent water, and even greater than 70 or 80 percent water. Typically the water level is from about 80 to 95 percent for this prewashed fungal biomass.

D. EXAMPLES

The invention will be further explained by the following non-limiting illustrative examples. Unless otherwise indicated, all amounts are expressed in parts by weight.

Example 1

Citric biomass was pretreated with a 4 percent aqueous sodium hydroxide (NaOH) solution in an autoclave at 120° C. for 1 hour. This step removed excess proteins and other undesirable materials. The biomass was then thoroughly washed with de-ionized water until its pH was approximately 7.0. This washed material was mixed with concentrated hydrochloric acid (HCl) and water to form a mixture of 10 to 15 percent HCl and 5 to 6 percent biomass, based upon dry weight of the biomass. This mixture was heated at reflux. Samples were taken from time to time, and the reaction analyzed with a high-pressure liquid chromatograph available from Dionex HPLC under the trade designation "DX-500".

Figure 2:
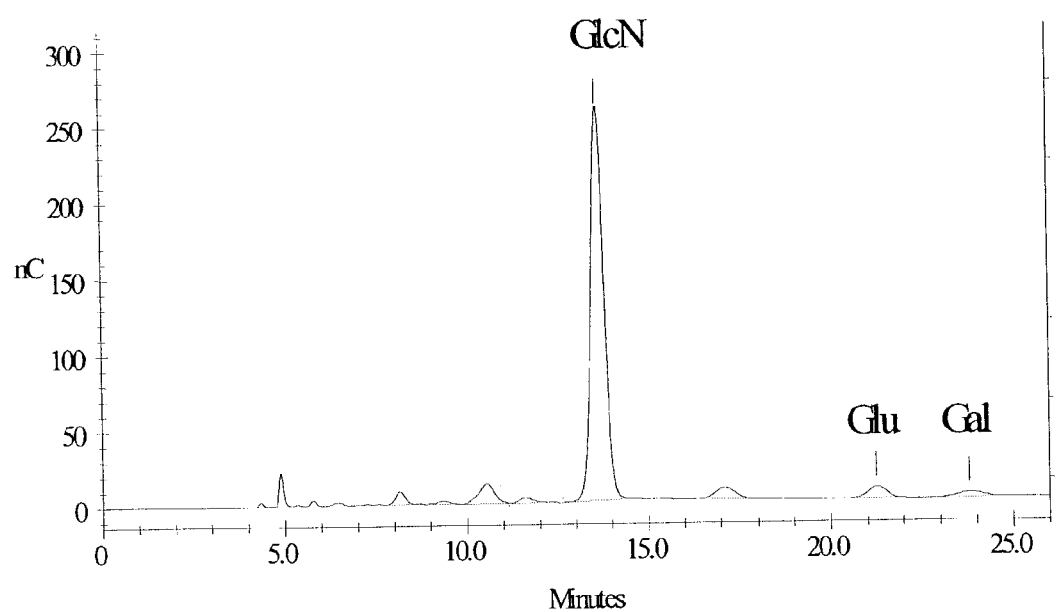
FIG. 2 is a chromatogram of glucosamine made in accordance with the invention.

The results are provided in FIG. 1, which shows a chart indicating glucosamine production, and shows that the glucosamine was increasingly produced as the reaction ran through 8 hours, but that the amount of glucose diminished after 4 hours. After 8 hours the glucosamine produced in the yield of 14 percent. A chromatogram of the product is shown in FIG. 2.

Figure 3:
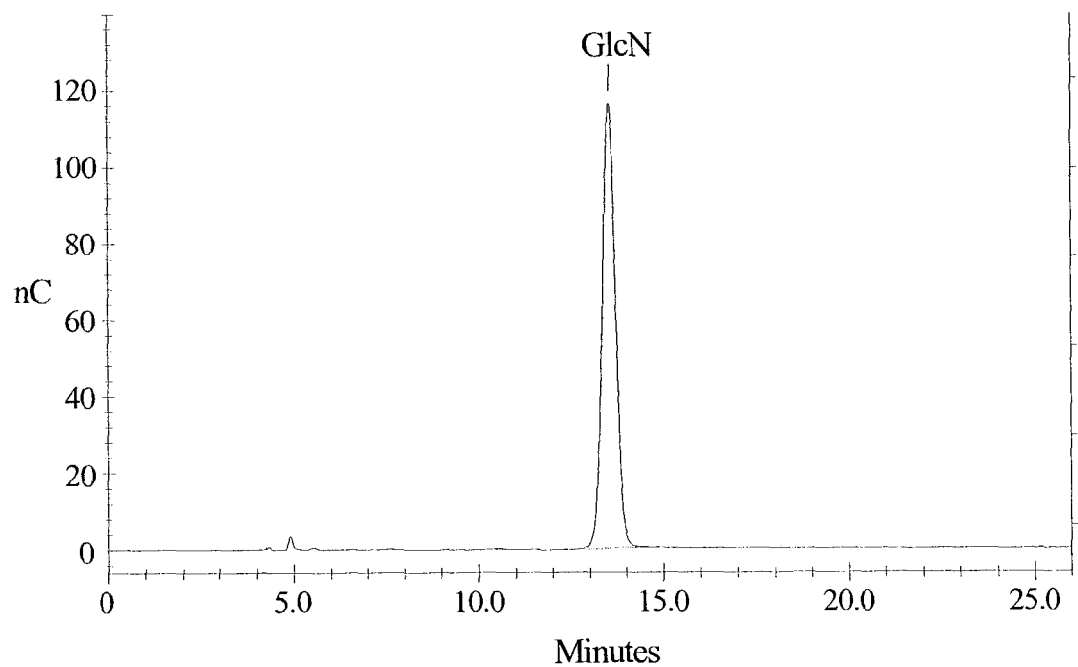
FIG. 3 is a chromatogram of glucosamine made in accordance with the invention.

Following reaction, the mixture was filtered, and the filtrate evaporated using a rotating evaporator manufactured by RotaVap to increase the glucosamine concentration of the solution. The final volume was reduced to about 10 to 20 ml. To this solution was added 20 ml of ethanol and the solution swirled to promote precipitation of glucosamine and enhance yield. These glucosamine precipitates were obtained by filtration and were further washed with alcohol until the color became white. FIG. 3 shows a chromatogram of the product, indicating greater than 97 percent glucosamine.

Example 2

Example 1 was repeated, but the pretreated biomass was maintained under reflux conditions for 13 hours. The resulting glucosamine was greater than 98 percent pure.

The foregoing detailed description and examples have been given for clarity of understanding only. No unnecessary limitations are to be understood from this description or examples. The invention is not limited to the exact details shown and described, for variations will be included within the invention defined by the claims.

We claim:

1. A method of obtaining glucosamine from fungal biomass, the method comprising the steps of:
    (a) providing the fungal biomass;
    (b) reacting the fungal biomass in an acidic solution with an acid concentration of greater than 5 percent by weight at a reaction temperature greater than 80° C. for a reaction period of at least 4 hours to convert chitin in the fungal biomass to glucosamine; and
    (c) separating the glucosamine from the acidic solution; wherein the method has a yield of glucosamine of greater than 50% of total chitin content of the fungal biomass.

2. The method of claim 1, wherein the step of separating the glucosamine comprises crystallization of the glucosamine from the acidic solution.

3. The method of claim 1, wherein the acid solution has an acid concentration of 5 to 25 percent by weight.

4. The method of claim 1, wherein the acid solution has an acid concentration of 5 to 50 percent by weight.

5. The method of claim 1, wherein the reaction temperature is above 80° C.

6. The method of claim 1, wherein the reaction period is from 4 to 25 hours.

7. The method of claim 1, wherein the separated glucosamine has a yield of greater than 50 percent of total chitin content of the fungal biomass and contains less than 5 percent glucose.

8. The method of claim 1, wherein the separated glucosamine contains less than 5 percent soluble sugars.

9. The method of claim 1, wherein the separated glucosamine is greater than 98 percent glucosamine based upon dry weight.

10. The method of claim 1, wherein the glucosamine is derived from *Aspergillus* sp., *Penicillium* sp., *Mucor* sp. and combinations thereof.

11. A method of obtaining glucosamine from fungal biomass, the method comprising the steps of:
    (a) providing fungal biomass;
    (b) pretreating the fungal biomass with an alkaline solution;
    (c) reacting the fungal biomass in an acidic solution with an acid concentration of greater than 5 percent by weight at a reaction temperature greater than 80° C. for a reaction period of at least 4 hours to convert chitin in the fungal biomass to glucosamine; and
    (d) separating the glucosamine from the acidic solution; wherein the method has a yield glucosamine of greater than 50% of total chitin content of the fungal biomass.

12. The method of claim 11, wherein greater than 50 percent of total chitin content of the fungal biomass is converted to glucosamine and the glucosamine separated from the acidic solution contains less than 5 percent glucose.

13. The method of claim 11, wherein the glucosamine separated from the acidic solution contains less than 20 parts per million heavy metals.

* * * * *

UNITED STATES PATENT AND TRADEMARK OFFICE
CERTIFICATE OF CORRECTION

| | |
|---|---|
| PATENT NO. | : 7,049,433 B2 |
| APPLICATION NO. | : 10/326549 |
| DATED | : May 23, 2006 |
| INVENTOR(S) | : Weiyu Fan et al. |

Page 1 of 1

It is certified that error appears in the above-identified patent and that said Letters Patent is hereby corrected as shown below:

<u>In the Claims:</u>

Column 8, line 24, "yield glucosamine" should be --yield of glucosamine--.

Signed and Sealed this

Sixth Day of November, 2007

JON W. DUDAS
*Director of the United States Patent and Trademark Office*